United States Patent [19]

Dobrilla

[11] Patent Number: 4,925,298

[45] Date of Patent: May 15, 1990

[54] ETCH PIT DENSITY MEASURING METHOD

[76] Inventor: Paolo Dobrilla, 60 Smithfield Ct., Basking Ridge, N.J. 07920

[21] Appl. No.: 228,492

[22] Filed: Aug. 5, 1988

[51] Int. Cl.$^5$ ............................................. G01N 21/55
[52] U.S. Cl. .................................... 356/30; 356/445; 356/448
[58] Field of Search ................ 356/30, 31, 445, 448, 356/237

[56] References Cited

U.S. PATENT DOCUMENTS

| | | | |
|---|---|---|---|
| 3,782,836 | 1/1974 | Fey et al. | 356/30 |
| 3,922,093 | 11/1975 | Dandliker et al. | 356/371 |
| 3,971,956 | 7/1976 | Jakeman et al. | 250/571 |
| 4,194,127 | 8/1980 | Schmidt | 250/572 |
| 4,505,585 | 3/1985 | Yoshikawa et al | 356/237 |
| 4,511,800 | 4/1985 | Harbeke et al. | 250/372 |
| 4,547,073 | 10/1985 | Kugimiya | 356/371 |
| 4,656,358 | 4/1987 | Divens et al. | 250/372 |

OTHER PUBLICATIONS

Dobrilla, *Materials Letters*, vol. 3, No. 7, May 1985, pp. 299–301.
Rees et al, *Material Letters*, vol. 4, No. 11, 12, Oct. 1986, pp. 455–457.
Toyoda et al., Defect Recognition and Image Processing in III-V Compounds, Montipellier, 1985, ed. J. P. Fillard (Elsevien, Amsterdam, 1985) pp. 141–147.

*Primary Examiner*—F. L. Evans

[57] ABSTRACT

A method for measuring and plotting the etch pit density on the surface of an etched monocrystalline test wafer is described. In accordance with the described method a beam of light is generated and focussed on the surface of a polished reference wafer. The wafer surface is oriented in a plane perpendicular to the beam of light. The intensity of light reflected normally from the reference wafer surface is measured to obtain a reference intensity $R_o$. Thereafter, the beam of light is focussed on the etched test wafer surface which is also oriented in a plane perpendicular to the beam of light. The intensity $R_e$ of light reflected normally from the etched test wafer surface is measured. The etch pit density on the test wafer surface is computer from the ratio of light intensity reflected from the test wafer to light intensity reflected from the reference wafer. The formula $EPD = -(1/Ap)\log(R_e/R_o)$, where EPD is etch pit density and AP is the average area of the etch pits is used. The computation of etch pit density is repeated for a plurality of locations on the test wafer surface. The locations are automatically determined by stepwise movement of the etched test wafer.

11 Claims, 8 Drawing Sheets

 
FIG. 7-1  FIG. 7-2

ETCH PIT DENSITY MEASURING METHOD

FIELD OF THE INVENTION

The present invention relates to etch pit density measurement. The method of the present invention is particularly suited to automatically measuring and mapping the surface density of etch pits on etched monocrystalline wafers such as polished galium arsenide wafers.

BACKGROUND OF THE INVENTION

The electrical properties of semiconductor substrates such as GaAs are a sensitive function of the number and distribution of dislocations in the material. Semi-insulating GaAs grown by the liquid encapsulated Czochralski method is emerging as a viable substrate for producing complex devices and integrated circuits. The number of dislocations in such material is an important parameter. Many GaAs users require substrates with a dislocation density lower than some specific limit. It therefore is of importance to be able to measure the dislocation density in the material For certain purposes, the spatial distribution of dislocations in the material is important, requiring an ability to map the variation of dislocation density through the material.

It is known in the art that dislocations in GaAs may be revealed by etching the sample with a suitable chemical. Dislocations that intersect the surface of the material are revealed as etch pits after etching. Typical etch pits formed by potassium hydroxide etching of GaAs are shown in FIG. 1. The number of such pits per unit surface area, or etch pit density, is a reliable indicator of the number of dislocations within the substrate. The pits assume a pattern reflecting slip planes in the crystal. (FIG. 2)

Etch pit density is commonly measured by visual pit counting under the microscope. The technique, as usually practiced, involves visual observation of a relatively small number of areas (say, nine) on the wafer and manual counting by a human operator. The technique is slow and inaccurate, principally due to fatigue of the operator.

A technique for measuring GaAs etch pit density (EPD) by monitoring optical reflectivity through measurement of the time required to get a standard exposure in a photomicrograph of the surface is known. [Dobrilla, Mat. Letters 3 (7,8) May 1985, 299] The technique is based on the principle that pits formed on GaAs by potassium hydroxide etching are substantially less reflective than the surrounding surface. Accordingly, the intensity of light reflected to the film in a camera equipped microscope can be approximated by a decreasing, linear function of the number of pits in the field of view of the objective. Consequently, the time required to get a correct exposure is proportional to the local, non-uniform etch pit density. A map of the etch pit density and a quantitative measurement of EPD at specific points can be obtained by shooting pairs of microphotographs with differing exposure times at each point.

Rees, Stirland and Bicknell [Mat. Lttrs. 4 (11,12) October 1986, 455] have shown that EPD is related to the fraction $FW_c$ of surface covered by etch pits and the area of each pit $A_p$ by $$EPD = -(1/A_p) \log (1 - FW_c).$$

A system for determining EPD by using a Vidicon camera to recognize etch pits has been described by Toyoda, Aota and Takahashi, in *Defect Recognition and Image Processing:* Montpellier, 1985, ed. J. P. Fillard (Elsevier, Amsterdam, 1985), 141. The system has a low spatial resolution and the measurement is much slower than the one here proposed.

It is old in the art to measure surface properties of materials by methods employing reflected or scattered light. Schmidt, U.S. Pat. No. 4,194,127, teaches an optical system for detecting and automatically plotting surface defects on polished single crystal semiconductor substrate wafers. The system employs an optical microscope to produce an image of the surface. The image is blurred by a translucent material and the light transmitted by the translucent material is then sensed by a light sensitive instrument such as a photomultiplier tube. Defects in the surface of the wafer appear bright in the microscope in contrast to the background. When the microscope is focussed on a defect, the output of the photomultiplier tube increases. The photomultiplier tube signal is amplified and fed to a plotter. A map of the defects is produced by moving the wafer-bearing microscope stage in the two orthogonal transverse directions in a stepwise manner.

Divens, et al. and Yoshikawa, et al. measure surface features such as photoresist lines, edges, cracks and pinholes by means of reflected laser beams as described in Divens, et al., U.S. Pat. No. 4,656,358 and Yoshikawa, et al., U.S. Pat. No. 4,505,585. The method of Divens, et al. involves focussing an ultraviolet laser beam on the surface and detecting the scattered and reflected light. The optical system includes a high numerical aperture objective close to the sample surface, two UV optical trains, and a UV detector. The sample is transversely moved under a stationary microspot provided by a tightly-focussed UV laser beam. The scattered and reflected light passes back through the objective of the microscope, through the second optical train to the UV detector. The UV detector provides a signal representative of the intensity of the scattered or reflected light. Plots of the intensity of reflected light as a function of transverse position of the sample provide accurate and reproducible profiles of the features being measured.

Yoshikawa et al. employ a system comprising a turntable on which the wafer is mounted, a laser beam directed onto the surface, a photo detector for detecting the light reflected from the surface, and electronics and a data processor to generate and record a defect signal when the laser beam falls on a surface defect.

An apparatus for examining and detecting macroscopic defects in the surfaces of polished semiconductor substrates is disclosed by Kugimiya, U.S. Pat. No. 4,547,073. The apparatus comprises a light source, a first optical means for converging the light to a parallel beam and projecting it onto the surface, and a second optical means for transporting the light reflected by the surface to a light receiving screen where millimeter sized defects are detected by specific shading patterns, lines, stripes or dots.

Methods of measuring the roughness of surfaces are taught by Jakeman et al., U.S. Pat. No. 3,971,956, and Dandliker et al., U.S. Pat. No. 3,922,093, wherein light is shone on the surface and the radiation scattered or reflected at oblique angles is detected and analyzed.

Yet another method of measurement of surface roughness, and amorphism, of polycrystalline silicon films is described in Harbeke, U.S. Pat. No. 4,511,800. The method involves observing the differential optical reflectance of a test surface and a surface of known minimal roughness. The respective intensities of the two reflected beams are detected and measured. The difference in intensities of the two reflected beams can be related to the surface roughness of the sample being examined. The device employs optical trains to focus one beam on the sample and the reflected beam on the detector, a beam chopper driven by a motor, control electronics, including a lock-in amplifier, and a logic unit for calculating the reflectance signal. The method measures the root mean square roughness of amorphous or polycrystalline semiconductor materials. Since there is no direct relation between surface roughness and etch pit density, the method is not capable of measuring etch pit density, nor is the method capable of measuring surface properties of single-crystal layers. The method would be overloaded by an attempted measurement of etch pit density.

All the prior art described above is capable only of revealing relatively rare defects on an otherwise perfect surface, measuring the departure of the sample from perfection. The present invention is intended to provide a means of reliably measuring a very large number of defects on a sample, namely. thousands of etch pits.

SUMMARY OF THE INVENTION

The invention is an automatic method, based on reflectivity measurements, that provides EPD values for etched monocrystalline wafers. The method enables the return of about 10,000 EPD values in less than an hour at locations uniformly distributed across the sample. The method requires as input parameter only a direct measurement of the average area of the etch pits. A beam of light is generated, suitably by employing the beam from a broad band halogen bulb. The beam of light is focussed normally on the etched test wafer surface as well as on a reference polished surface. The focussing may be done by a microscope objective. The light reflected normally from the wafer is directed by a beam train to a photodetector, such as a silicon photodetector, whose output may be fed into a preamplifier followed by a lock-in amplifier. A reference signal is provided to the lock-in amplifier, preferably by a mechanical beam chopper in the beam train. The intensity of the light reflected from the reference wafer yields a reference intensity $R_o$ while the intensity of the light reflected from the etched test wafer yields intensity $R_e$. These intensities may be digitized by digitizing the DC output of the lock-in amplifier with a desktop computer. The computer also computes the EPD value, by employing the relation $$EPD = -(1/A_p) \log (R_e/R_o)$$

where $A_p$ is the average etch pit area. The test wafer is suitably moved stepwise in a plane perpendicular to the light beam by motors under computer control so that a map of the EPD values at a preselected number of points on the test wafer is automatically generated.

BRIEF DESCRIPTION OF THE DRAWINGS

FIG. 7 shows etch pits on wafers used in FIG. 6.

DESCRIPTION OF THE PREFERRED EMBODIMENT

Figure 1:
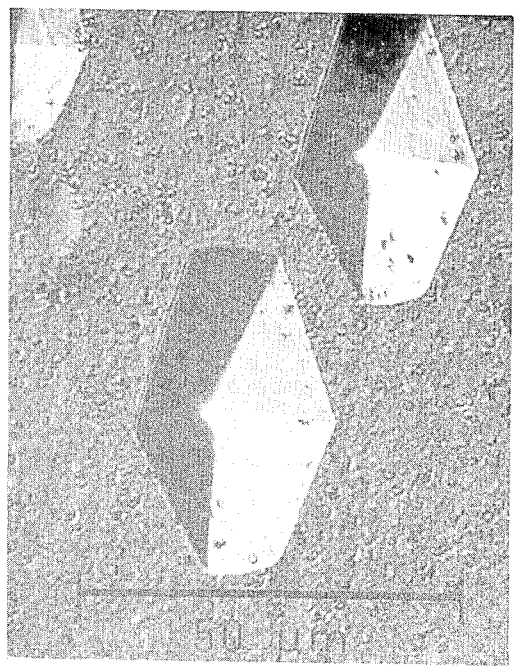
FIG. 1 is a photomicrograph of KOH-produced etch pits on the (100) plane of GaAs.
Figure 2:
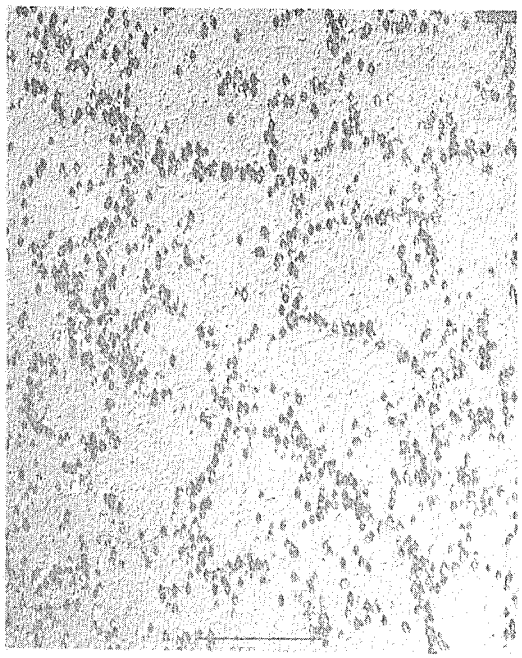
FIG. 2 is an example of the cellular pattern assumed by dislocations (etch pits) in LEC grown GaAs.
Figure 3:
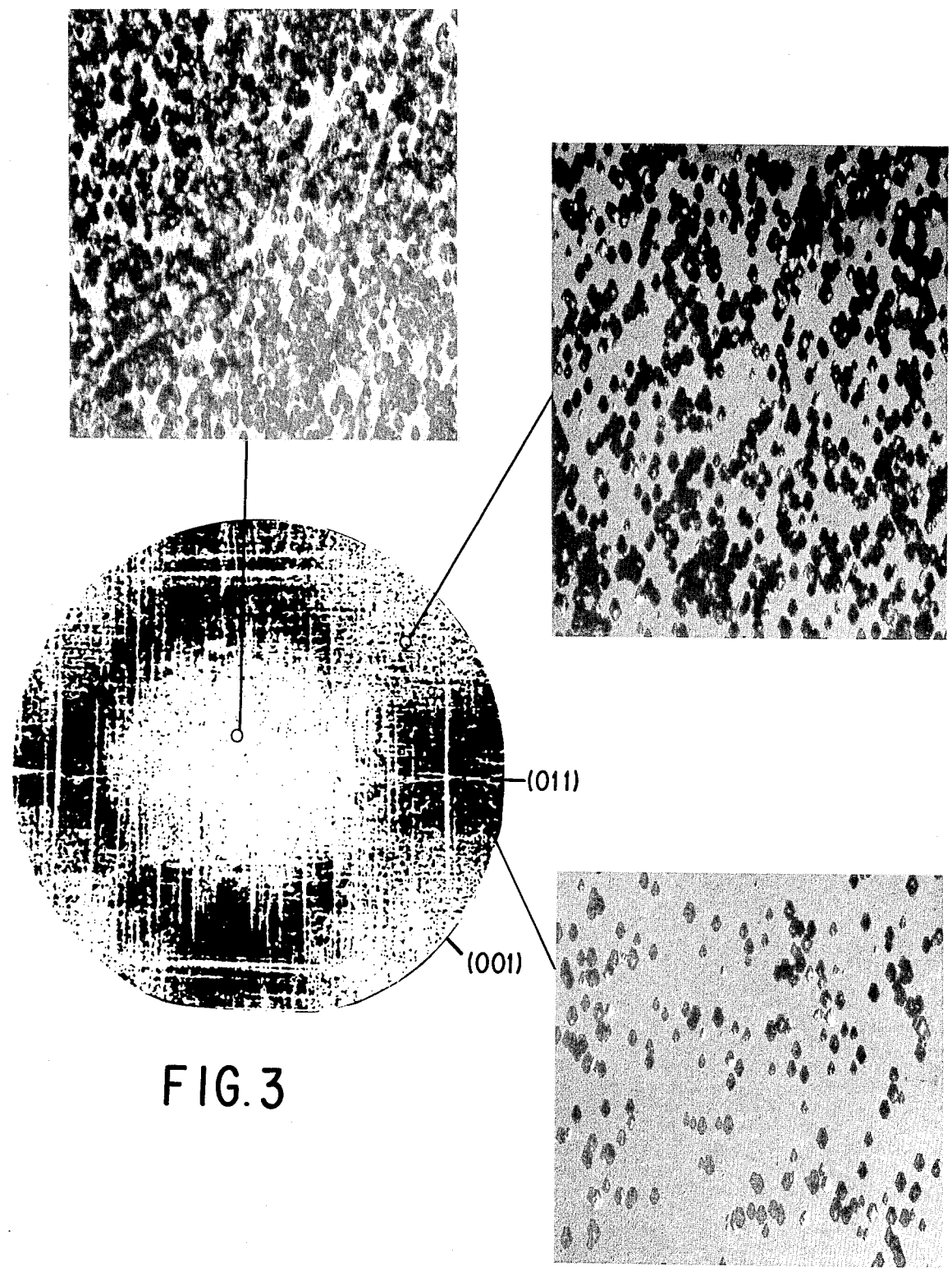
FIG. 3 is a contact photocopy of a KOH etched (100) GaAs wafer. Areas of higher EPD appear lighter than areas of low EPD. The crystallographic nomenclature used here is kept in all the figures.
Figure 4:
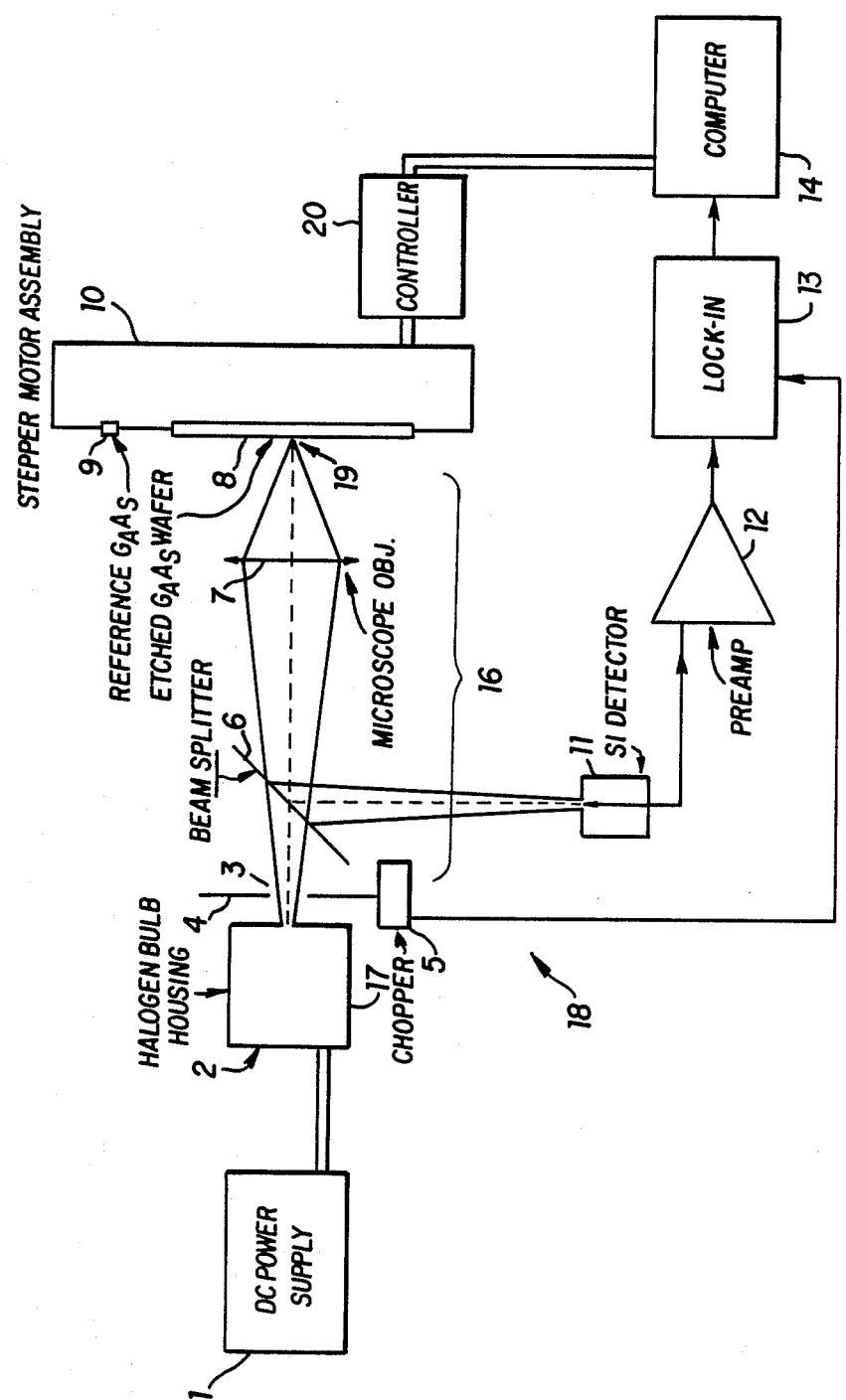
FIG. 4 is a schematic of the EPD measuring system.

FIG. 4 is an isometric schematic of a wafer measurement instrument 15 used for automatically measuring and plotting etch pit density (EPD) on GaAs wafers at 10,000 locations across the face of the wafer. EPD may vary substantially across the wafer, as seen in FIG. 3. The basic components of the instrument 15 are a stepper motor assembly 10, an optical system 16, and a computer/plotter 14.

The optical system 16 includes a broad band halogen bulb 17 in a bulb housing 2, such as an Oriel bulb housing. The halogen bulb 17 is powered by a stabilized DC current supply 1, such as an LH Research power supply, model TMF 31/2. The bulb 17 produces a beam of light that is focussed by a 4× microscope objective (NA=0.1) 7, such as a Spindler & Hoyer microscope body and objective, onto the etched surface of the test wafer to be examined 8, forming a beam spot 19 whose diameter is small compared to the diameter of the test wafer 8 but large compared to the size of an etch pit so that the beam spot 19 covers a large number of etch pits. The beam spot should be smaller in diameter than the spacing between adjacent measurement positions so as not to overlap adjacent beam spot areas. The test wafer is prepared by etching with molten KOH by the ASTM standard method described in ASTM F47-84. Light reflected from the surface of the wafer 8 passes through the objective 7 to a beam splitter 6, such as a Melles Griot pellicle beam splitter, and is reflected to a silicon photo detector 11, such as a Hamamatzu Si detector. The output of the Si detector 11 is fed into a preamplifier 12 followed by a lock-in amplifier 13. The preamplifier 12 may be an EG&G preamplifier, model 189, and the lock-in amplifier 13 may be an EG&G lock-in amplifier, model 186A. The DC voltage from the lock-in amplifier 13 is digitized (12 bit A/D conversion) by an IBM 9000 desktop computer 14 which also computes the EPD value by the procedure described below.

A reference wafer of GaAs 9 which has been polished is removably affixed upon the stage of a stepper motor assembly 10 such as a Daedal stepper motor, model 4404, disposed in about the same plane as the etched wafer 8. The stepper motor assembly 10 is under the control of computer 14 through a stepper motor controller 20 such as Daedal controller model PC 400-Z. The wafer to be inspected 8 may be moved in the plane perpendicular to the light beam 16 by the stepper motor assembly 10 under the control of the controller 20, which is controlled by the IBM 9000 computer 14. The controller 20 translates the instructions of computer 14 into movements of the stepper motor assembly 10. Stepper motors require, and are generally sold with, an appropriate controller.

A reference signal to the lock-in is provided by a mechanical chopper 5 that blocks the light at a frequency of about 670 Hz. An EG&G light chopper, model 1254, may be used. The frequency is arbitrary, but should be chosen to be different from that of the predominant noise generation.

The reference wafer 9 and the wafer to be examined 8 are each removably affixed to the stage of the stepper motor assembly 10 by sample holders such as NRC sample holder model ALM4.

Figure 5:
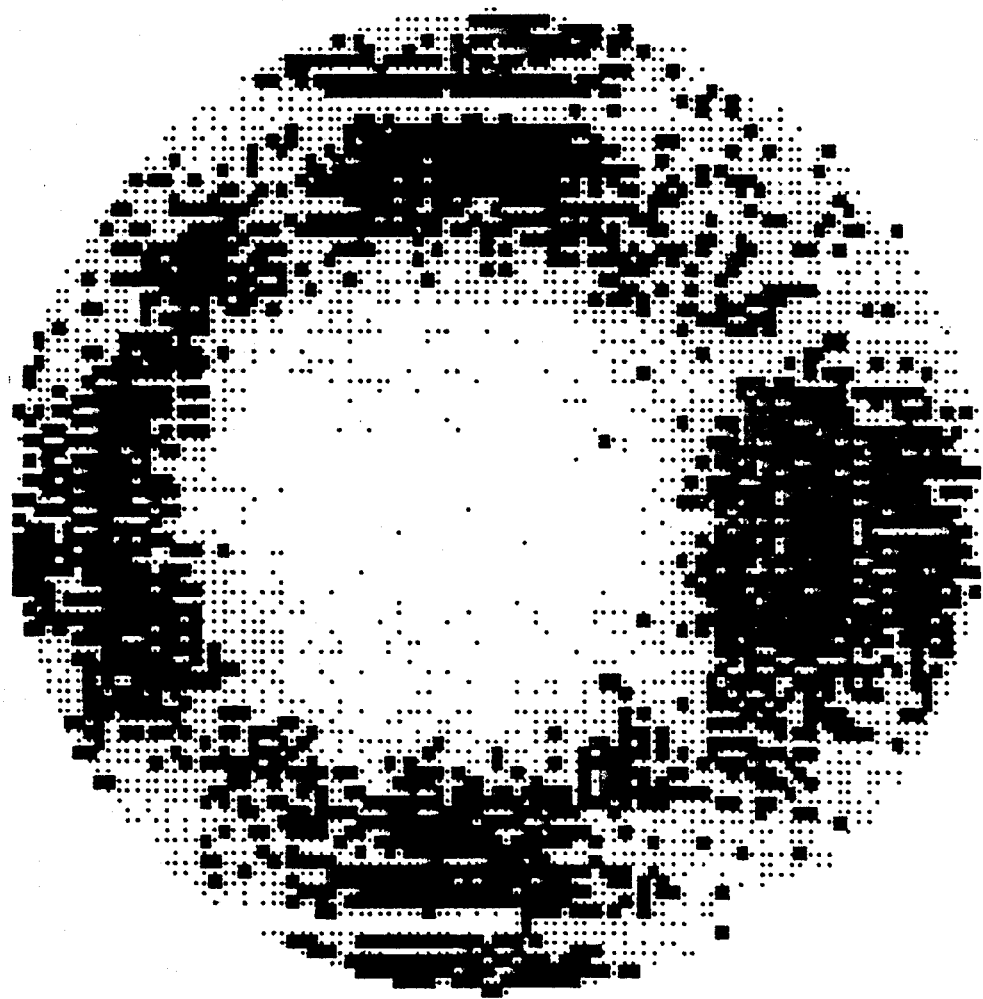
FIG. 5 is a reflectivity map for the same wafer as in FIG. 3. Comparing this to FIG. 3, it can be seen that low EPD areas are more reflecting (dark pixels) than areas of higher etch pit density.

The measurement is carried out in the following way. First the polished reference sample 9 is placed in the beam spot 19 of the light beam. This provides a reference value for the reflectivity of "clean" GaAs. This piece of GaAs is placed in about the same plane as the etched wafer 8 to be measured. Any small deviation from this plane, which would show up as reduced reference reflectivity, is taken into account by the program that handles all the measurement. The program mutiplies the uncorrected reflectivity of the test wafer by a correction factor determined by inserting a polished wafer in place of the test wafer and measuring its uncorrected reflectivity. The correction factor is that number which, when multiplied by the uncorrected reflectivity of the polished wafer, makes the reflectivity of the polished wafer unity. Let the DC voltage from the lock-in 13 corresponding to the intensity of the light reflected by the polished GaAs be $R_o$. Then the etched wafer 8 is raster scanned at steps of 0.48 mm for a 2-inch wafer, or 0.70 mm for a 3-inch wafer, while the signal from the silicon detector 11 is recorded at every location. If the reflected signal from the etched wafer is denoted by $R_e$, the computer 14 memorizes the ratio $R_e/R_o$ for all the locations on the sample. FIG. 5 shows a typical reflectivity map of a GaAs wafer obtained by this method.

The spacing between adjacent measured locations is chosen so that most of the wafer surface is mapped when a grid of 99×99 points is optimally superimposed onto it. This grid can obviously be made more or less dense by changing the software. The density of the grid is limited by the requirement that the spacing between adjacent positions on the wafer must be larger than the diameter of the beam spot produced at the focus of the microscope objective 7. The optimum spacing is a distance equal to the beam diameter.

The time required to scan all the positions on the wafer 8 depends upon the delay inserted between successive steps; short delays make the measurement faster but reduce the resolution of the system due to the finite response time of the lock-in. The longer the interval between steps, the greater is the instrument noise rejection. A delay time producing a total run time of slightly less than one hour has been found to be the best compromise between accuracy and speed.

Etching of GaAs crystals grown by the liquid encapsulated Czochralski method produces etch pits that are concavely facetted in such manner that for light incident perpendicular to the surface, the intensity of light reflected from the pit in a direction perpendicular to the surface is negligible compared to that of light reflected from the surrounding flat surface.

To obtain the relationship between reflectivity and etch pit density for arbitrary etch pit density, suppose there are N pits in the field of view FW of the microscope objective. Then the fraction of the field of view that is covered by pits is $$FW_c(N) = NA_p/FW = EPD\, A_p \quad (1)$$

where $A_p$ is the average area of the pits, since N/FW=EPD. Supposing for simplicity that the pit reflectivity $R_p$ is negligible with respect to polished GaAs reflectivity $R_o$, the total reflectivity of the surface comprised in FW is $$R_e = R_o(1-FW_c) = R_o(1-EPD\, A_p) \quad (2)$$

or $$R_e/R_o = (1-EPD\, A_p) \quad (3)$$

This simple model does not take into account the fact that pits are often overlapping each other, especially at high EPD.

To model the effect on reflectivity of an arbitrary etch pit density, for conditions where some etch pits do not overlap, others are contiguous with their neighbors, and still others may overlap, such as those in FIG. 7, begin with N pits in the FW of the objective. Then again we can write $$FW_c(N) = NA_p/FW = EPD\, A_p \quad (4)$$

Now consider adding DN more pits in the same FW, so that the coverage becomes $$FW_c(N+DN) = NA_p/FW + P(DNA_p/FW) \quad (5)$$

where P is the probability that the new DN pits are situated in a previously uncovered area of FW. (If DN falls into a previously covered area of FW, the quantity $FW_c$ does not change.)

Now $$P = 1 - FW_c(N) = 1 - NA_p/FW \quad (6)$$

and $$FW_c(N+DN) = NA_p/FW + DNA_p/FW - NDNA_p^2/FW^2 \quad (7)$$

Then we can write, in the limit DN→0, $$[FW_c(N+DN) - FW_c(N)]/dN \equiv \frac{dFW_c}{dN} = \quad (8)$$
$$[NA_p/FW + DNA_p/FW - NDNA_p^2/FW^2 - NA_p/FW]/DN =$$
$$A_p/FW - NA_p^2/FW^2 = (A_p/FW)(1 - NA_p/FW) =$$
$$(A_p/FW)(1 - FW_c(N))$$

or $$\frac{dFW_c}{dN} = \frac{A_p}{FW}(1 - FW_c) \quad (9)$$

Equation (9) is a differential equation for $FW_{c(N)}$ whose solution is $$FW_c = 1 - \exp(-NA_p/FW) \quad (10)$$

satisfying the condition $FW_c(N=0)=0$. Equation (10) can be rewritten as $$FW_c(EPD) = 1 - \exp(-EPD\, A_p) \quad (11)$$

At this point the reflectivity of the surface in FW will be:

$$R_e(EPD) = R_o(1 - FW_c) + R_p FW_c \quad (12)$$

or $$R_e/R_o = (1 - FW_c) + FW_c(R_p/R_o) = (1 - FW_c) \quad (13)$$

neglecting the factor $R_p/R_o$. In view of results obtained, this approximation seems to be justified.

Inserting Equation (11) in (13) we obtain $$R_e/R_o = \exp(-EPD\ A_p) \quad (14)$$

which can be inverted to yield EPD as a function of the measured quantity $R_e/R_o$:

$$EPD = -(1/A_p)\log(R_e/R_o) \quad (15)$$

This result can also be derived by substituting Equation (2), in the form $$R_e = R_o(1 - FW_c),$$

or Equation (13), in the form $$R_e/R_o = (1 - FW_c),$$

into the relation $$EPD = -(1/A_p)\log(1 - FW_c)$$

given by Rees, Stirland and Bicknell [Mat. Lettrs. 4 (11,12) October 1986, 455].

From Equation (15) it can be seen that the only adjustable parameter is the average etch pit area. If the etching process is controlled to a good degree, this parameter can be measured once and for all; otherwise its value must be verified prior to the measurement, by actually measuring a number of pits' sizes at the microscope and taking an average.

Figures 1, 6:
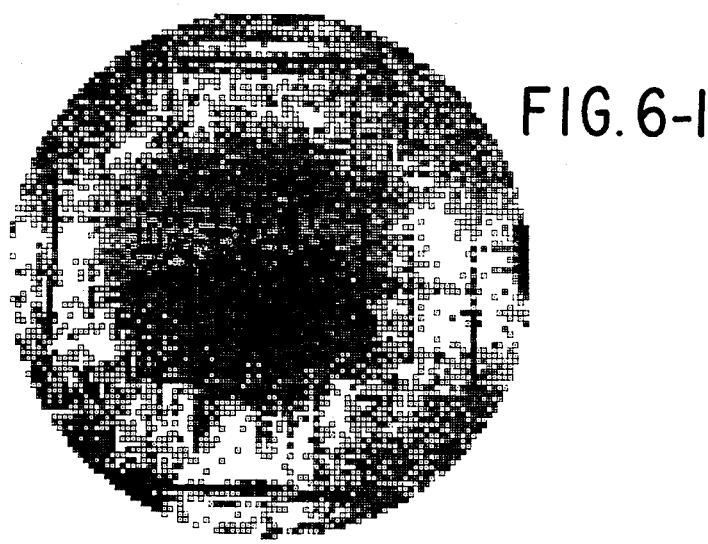
FIG. 6 shows EPD maps, obtained with the system here described, for 2" wafers cut from different crystals.
Figures 2, 6:
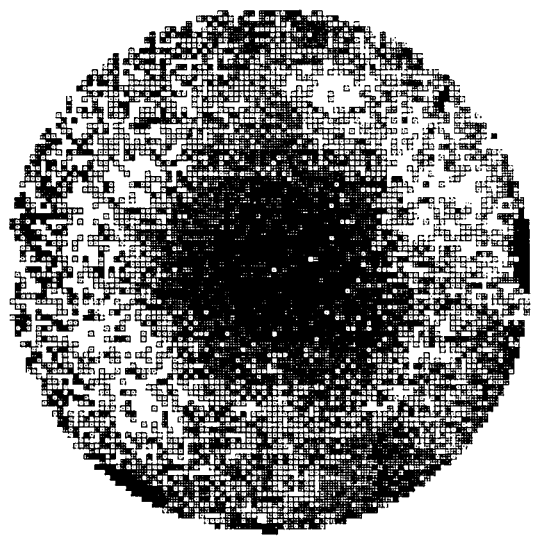
Figures 3, 6:
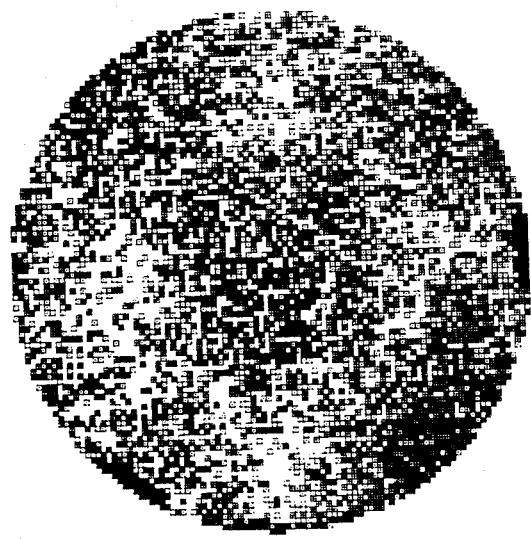
Figures 1, 8:
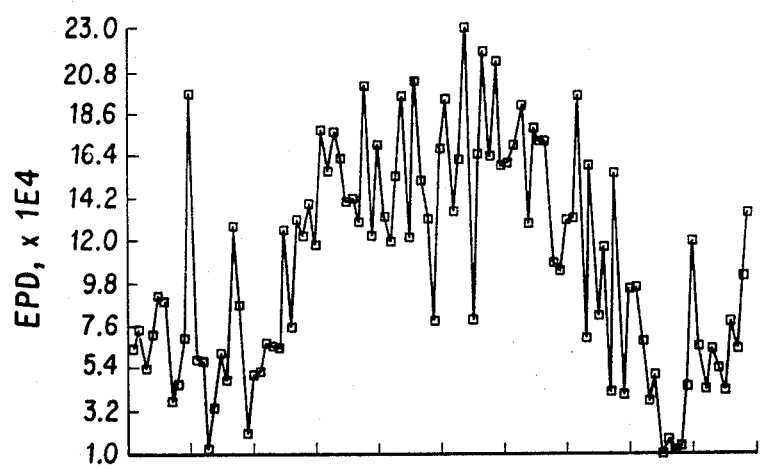
FIG. 8 compares EPD values obtained by the method described here with EPD values obtained by visual evaluations.
Figures 2, 8:
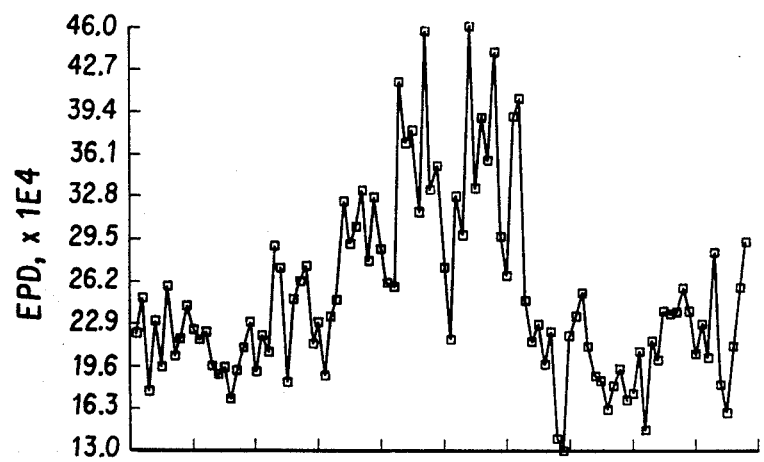
Figures 3, 8:
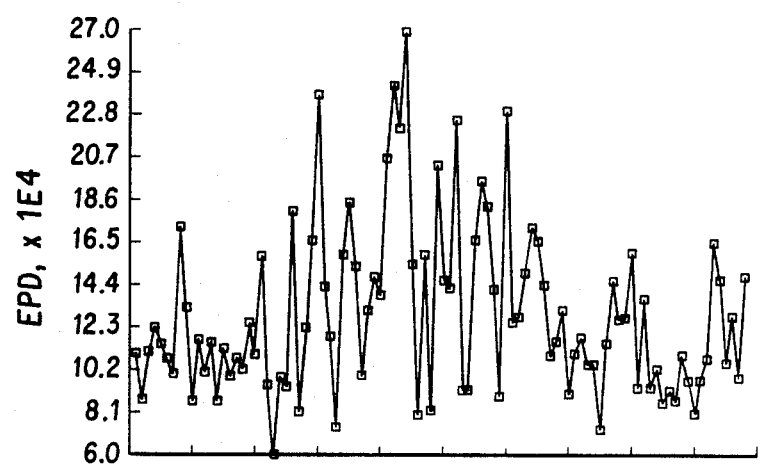

The method measures EPD values at each point on the grid. A typical result is shown in FIG. 6. Ideally, a calibration of the system should be performed by verifying by manual measurement with the microscope the etch pit density at the same locations that are examined by the light beam. A comparison of EPD values measured by the described method with those measured manually at slip lines (that have extremely high EPD) and very localized areas of low EPD shows that the agreement between the automatically and visually calculated EPD is better that 10 percent for EPD ranging between $10^4$ and $3.1 \times 10^5$ cm$^{-2}$. (FIG. 8) The system can reliably provide quantitative maps of EPD distribution in GaAs wafers with a very limited amount of input data (a single measurement of etch pit surface area) and practically no training of the operator, since the system is completely under computer control. The setup is not sensitive to secondary—and often uncontrollable—parameters, such as the dimensions of the pits and the roughness of the wafer surface around the pits.

As is evident from the foregoing, various modifications can be made without departing from the spirit of the invention. It is not intended to limit the invention to the details heretofore recited, the invention being defined in the claims which follow.

I claim:

1. A method for measuring the etch pit density on the surface of an etched monocrystalline test wafer and plotting said density at numerous locations on said surface, comprising:
   generating a beam of light;
   focussing said beam of light on a polished reference wafer surface oriented in a plane perpendicular to said beam of light;
   measuring the intensity of light reflected normally from said reference wafer surface to obtain a reference intensity $R_o$;
   thereafter, focussing said beam of light on said etched test wafer surface oriented in said plane;
   measuring the intensity $R_e$ of light reflected normally from said etched test wafer surface;
   computing the etch pit density on said test wafer surface from the ratio of said intensity to said reference intensity by employing the relation $EPD = -(1/A_p)\log(R_e/R_o)$, where EPD is etch pit density and $A_p$ is the average area of the etch pits; and
   repeating the computation of etch pit density at a plurality of locations on said test wafer surface automatically determined by stepwise movement of said etched test wafer in the plane perpendicular to said beam of light.

2. The method of claim 1, wherein said beam of light is generated by:
   producing a DC current from a stabilized DC power supply;
   and generating a beam of light from a broad band halogen bulb powered by said power supply.

3. The method of claim 1, wherein the light reflected from said etched test wafer surface and from said reference wafer surface is conducted to a light-to-electric converter.

4. The method of claim 3, wherein said conducting is effected by a pellicle beam splitter.

5. The method of claim 4, wherein the output of the light-to-electric converter is first fed into a preamplifier and then into a lock-in amplifier having a DC output.

6. The method of claim 5, wherein a reference signal is provided to the lock-in amplifier by a mechanical beam chopper.

7. The method of claim 6, wherein said beam chopper blocks the light at a frequency of about 670 Hz.

8. The method of claim 5, wherein the DC output of said lock-in amplifier is digitized and said digitized output is used for each computation of etch pit density.

9. The method of claim 3, wherein said light-to-electric converter is a silicon photodetector.

10. The method of claim 2, wherein said beam of light from said broad band halogen bulb is focussed by passing said beam of light through a focussing optical element.

11. The method of claim 10, wherein the focussing optical element is a microscope objective.

* * * * *